(12) United States Patent
Satoh et al.

(10) Patent No.: US 6,706,763 B1
(45) Date of Patent: Mar. 16, 2004

(54) O-ANISAMIDE DERIVATIVES

(75) Inventors: Hiroya Satoh, Oyama (JP); Masakatsu Komuro, Nogi-machi (JP); Koji Murakami, Oyama (JP); Katsuya Awano, Oyama (JP)

(73) Assignee: Kyorin Pharmaceutical Co., Ltd., Tokyo (JP)

( * ) Notice: Subject to any disclaimer, the term of this patent is extended or adjusted under 35 U.S.C. 154(b) by 0 days.

(21) Appl. No.: 10/070,425

(22) PCT Filed: Sep. 1, 2000

(86) PCT No.: PCT/JP00/05950

§ 371 (c)(1), (2), (4) Date: Mar. 18, 2002

(87) PCT Pub. No.: WO01/21578

PCT Pub. Date: Mar. 29, 2001

(30) Foreign Application Priority Data

Sep. 17, 1999 (JP) ............................................. 11/263070

(51) Int. Cl.[7] ................... A61K 31/195; C07C 229/00; C07C 235/00; C07C 237/00; C07C 323/00
(52) U.S. Cl. ................... 514/562; 514/563; 562/426; 562/430; 562/442; 562/451; 564/152; 564/154; 564/156
(58) Field of Search ................... 562/442, 426, 562/430, 451; 514/562, 563; 564/152, 154, 156

(56) References Cited

U.S. PATENT DOCUMENTS 5,948,803 A * 9/1999 Maeda et al.
6,001,862 A * 12/1999 Maeda et al.
6,030,990 A * 2/2000 Maeda et al.
6,147,101 A * 11/2000 Maeda et al.
6,506,797 B1 * 1/2003 Nomura et al.

FOREIGN PATENT DOCUMENTS

WO 97/31907 9/1997

* cited by examiner

*Primary Examiner*—Johann Richter
*Assistant Examiner*—Paul A. Zucker
(74) *Attorney, Agent, or Firm*—Oblon, Spivak, McClelland, Maier & Neustadt, P.C.

(57) ABSTRACT

O-anisamide compounds and their addition salts effective for the prevention and/or therapy of metabolic diseases such as hyperlipidemia and diabetes, in which peroxisome proliferator-activated receptor (PPAR) being intranuclear receptor, in particular, human PPAR participates, as agonistic drugs thereon, and processes for preparing them, wherein the o-anisamide compounds are represented by a general formula (1)

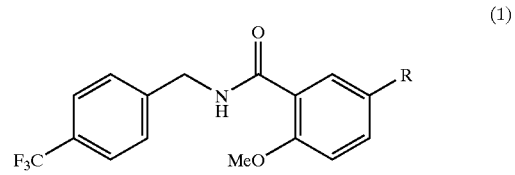

(1)

[wherein R denotes a carboxyl group, carboxymethyl group or CH$_2$CHXCOY (here X denotes a mercapto group or S(O)nMe (n=0, 1 or 2) and Y denotes an amino group or hydroxyl group)], their medicinally acceptable salts, and their hydrates.

16 Claims, No Drawings

O-ANISAMIDE DERIVATIVES

This application is a 371 of PCT/JP00/05950, filed Sep. 1, 2000.

TECHNICAL FIELD

The present invention relates to o-anisamide derivatives effective for the prevention and/or therapy of metabolic diseases such as hyperlipidemia and diabetes, in which peroxisome proliferator-activated receptor (PPAR) being intranuclear receptor, in particular, human PPAR participates, as agonistic drugs thereon, their addition salts, processes for preparing them, and medicinal compositions containing these compounds.

BACKGROUND TECHNOLOGIES

The peroxisome proliferator-activated receptor (PPAR) is a ligand-dependent transcription factor that belongs to intranuclear receptor superfamily similarly to steroid receptor, retinoid receptor, thyroid receptor, etc., and three isoforms (α type, β(or δ) type and γ type) with different histological distribution have been identified hitherto in human and various animal species (Proc. Natl. Acad. Sci., 1992, 89, 4653). There among, the PPARα is distributed in the liver, kidney, etc. with high catabolic capacity for fatty acids and, particularly in the liver, high expression is recognized (Endocrinology, 1995, 137, 354), positively or negatively controlling the expressions of genes relevant to the metabolism and the intracellular transport of fatty acids (e.g. acyl CoA synthetic enzyme, fatty acid-binding protein and lipoprotein lipase) and apolipoprotein (AI, AII, CIII) genes relevant to the metabolisms of cholesterol and triglyceride. Moreover, the PPARγ is highly expressed in the fat cells and takes part in the differentiation of fat cells (J. Lipid Res., 1996, 37, 907), and so on. In such way, each isoform of PPAR is fulfilling a specific function in the particular organs and tissues.

Additionally, it is reported that a knock-out mouse of PPARα exhibits hyper triglyceridemia with ageing and becomes obesity mainly by increased white adipocytes (J. Biol. Chem., 1998, 273, 29577), hence the relevance between activation of PPARa and lowering action of lipids (cholesterol and triglyceride) in blood is suggested strongly. Similarly, it is ascertained that the major intracellular target proteins of Troglitazone, Pioglitazone and Rosiglitazone being thiazolidine-2,4-dione derivatives that exhibit blood glucose-lowering action and improving action on hyperinsulinemia are PPARγs, and they increase the transcriptional activity of PPARγ (Endocrinology, 1996, 137, 4189, Cell., 1995, 83, 803 and 813). Hence, the relevance between activation of PPARγ and glucose-lowering action is suggested strongly.

When considering such functions of transcriptional factor called PPAR, for a compound that activates human PPAR, medicinal use aiming at the lowering action of lipids (cholesterol and triglyceride) in blood and/or the blood glucose-lowering action can be expected.

For compounds having an affinity to PPARα as ligands of PPARα, eicosanoides, in particular, 8-hydroxyeicosatetraenoic acid (8-HETE) and 8-hydroxyeicosapentaenoic acid (8-HEPE) are reported (Proc. Natl. Acad. Sci., 1997, 94, 312).

However, these endogenous unsaturated fatty acid derivatives are unstable and difficult to be offered as medicinal drugs, and, at the same time, they have different structure from the inventive compounds. Moreover, compounds having agonistic action on PPARα are reported in WO-97/25042, WO-97/36579, etc., but all of these have different structure from the inventive compounds and, at the same time, the effect of agonistic action is also never satisfied in strength. For compounds having agonistic action on PPARγ, a series of thiazolidine-2,4-dione derivatives are known in Japanese Unexamined Patent Publication Nos. Sho 60-51189, Sho 61-267580, Hei 1-131169, etc. However, all have different structure from the inventive compounds.

It is pointed out that the hyperlipidemia and the diabetes are principal diseases that modern times have to tackle and, at the same time, these become risk factors and link up with the atherosclerotic diseases, in particular, coronary atherosclerotic disease. Hence, from a viewpoint of the therapy or prevention thereof, the development of a therapeutic drug for metabolic diseases being effective and having high safety based on new action is desired strongly.

DISCLOSURE OF THE INVENTION

As a result of diligent studies paying an attention to the specific roles on the lipometabolism, adipocyte differentiation, of human PPAR, and aiming at the creation of structurally novel drug with high effectiveness and safety as a therapeutic drug for metabolic diseases, the inventors have found that o-anisamide derivatives represented by a following general formula (1) have excellent agonistic action on human PPAR and are useful as therapeutic drugs for metabolic diseases, leading to the completion of the invention.

Namely, the invention relates to o-anisamide derivatives represented by a general formula (1)

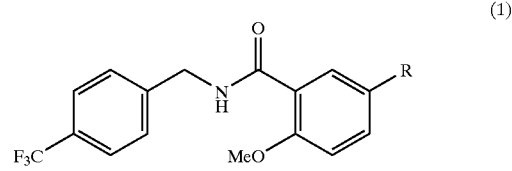

(1)

[wherein R denotes a carboxyl group, carboxymethyl group or $CH_2CHXCOY$ (here X denotes a mercapto group or $S(O)nMe$ (n=0, 1 or 2) and Y denotes an amino group or hydroxyl group)], their medicinally acceptable salts and their hydrates.

The medicinally acceptable salts of the compounds represented by the general formula (1) in the invention are of common use and metal salts, for example, alkali metal salts (sodium salt, potassium salt, etc.), alkaline earth metal salts (calcium salt, magnesium salt, etc.) and aluminum salt are mentioned.

Moreover, the compounds, R being $CH_2CHXCOY$, in the general formula (1) of the invention include optically active substances based on asymmetric carbon, and further, in the case of X being SOMe group, they include stereoisomers based on their three dimensions, but all of these isomers and mixtures are to be included in the scope of the invention.

According to the invention, compounds (1), being said general formula (1), can be prepared through processes shown in following diagram.

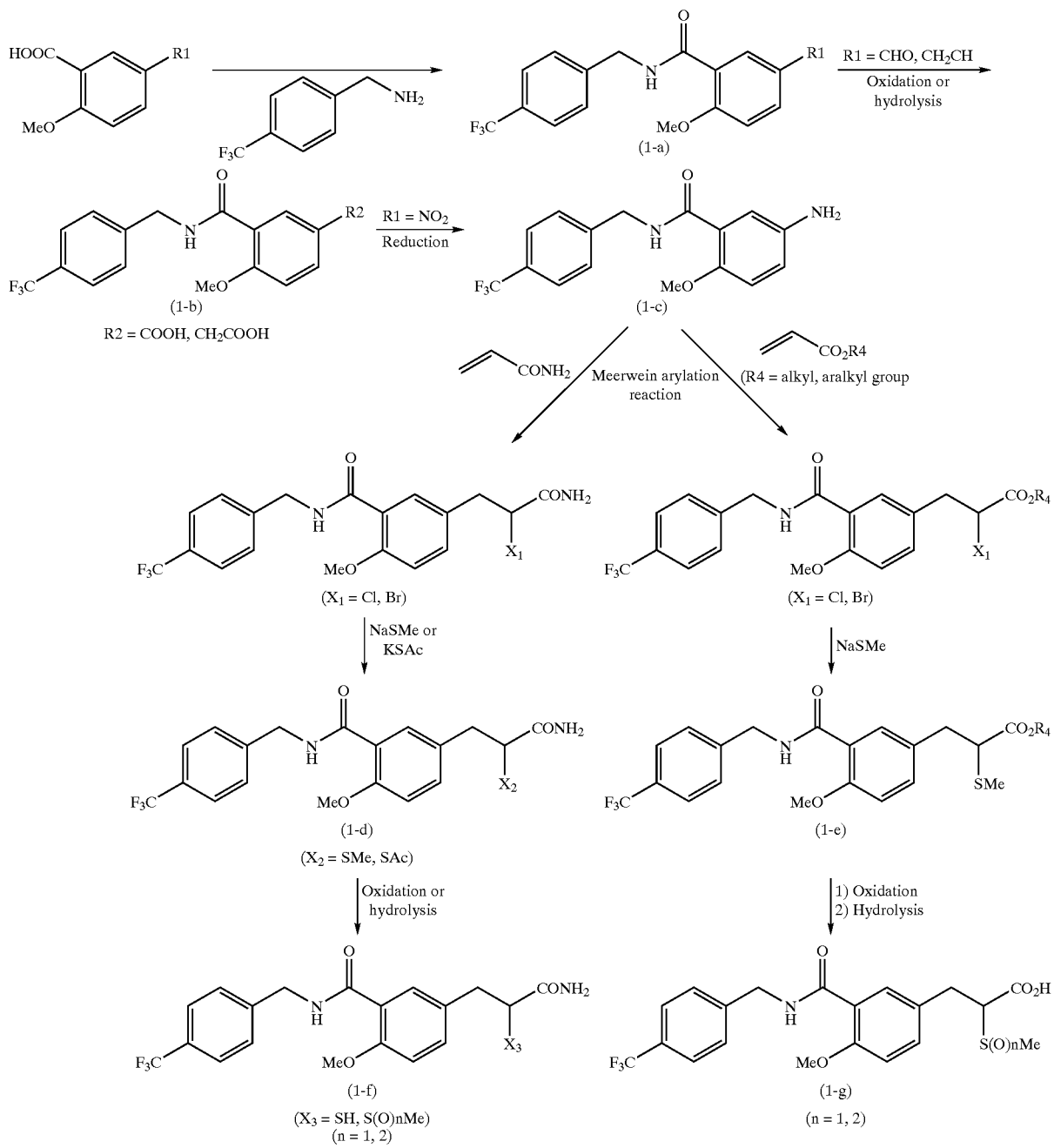

Namely, compounds represented by a general formula (1-a) can be prepared by condensation, leaving carboxyl group as it is or after converted it to reactive derivative according to usual method in the process shown in the diagram above.

In the case of conducting the reaction by leaving carboxylic acid as it is, the reaction can be performed in an inert solvent such as methylene chloride, chloroform, dioxane or N,N-dimethylformamide in the presence of condensing agent in the presence or absence of base, and further in the presence or absence of additive. As the condensing agent, for example, dicyclohexylcarbodiimide, 1-[3-(dimethylamino)propyl]-3-ethylcarbodiimide hydrochloride, diethyl cyanophosphonate, diphenylphosphoryl azide, carbonyldiimidazole or the like can be mentioned. As the base, for example, alkali metal hydroxide such as sodium hydroxide, alkali metal carbonate such as potassium carbonate, or organic base such as pyridine or triethylamine can be mentioned. As the additive, N-hydroxybenzotriazole, N-hydroxysuccinimide, 3,4-dihydro-3-hydroxy-4-oxo-1,2,3-benzotriazine or the like can be mentioned.

In the case of using reactive derivative, the reaction can be performed in an inert solvent such as methylene chloride, chloroform, dioxane or N,N-dimethylformamide in the presence or absence of, for example, alkali metal hydroxide such as sodium hydroxide, alkali metal carbonate such as potassium carbonate, or organic base such as pyridine or triethylamine as a base. As the reactive derivative, acid chloride, acid bromide, acid anhydride, carbonylimidazole or the like can be mentioned. The reaction can be performed at a reaction temperature of −20° C. to 100° C., preferably 0° C. to room temperature.

Compounds represented by a general formula (1-b) can be prepared by oxidation using usual oxidizing agent, followed by, if need be, hydrolysis. Namely, in the case of R1 being formyl group, the reaction can be performed using usual oxidizing agent, for example, chromium oxide, potassium permanganate, silver oxide or peroxide, but the oxidation using Jones reagent that uses chromic acid is preferable. The reaction temperature is preferable to be under cooling with ice to room temperature. In the case of R1 being cyanomethyl group, the reaction can be performed using peroxide, acid and base, but it is preferable to use acid such as concentrated sulfuric acid or concentrated hydrochloric acid, hydrogen peroxide or the like to convert to carbamoylmethyl group, followed by hydrolysis using base such as sodium hydroxide or potassium hydroxide. The reaction can be performed at a reaction temperature of 50° C. to refluxing temperature of solvent in a reaction solvent of alcohol-water system (methanol, ethanol or the like).

Compound, $X_2$ being methylthio group in a general formula (1-d), and compounds represented by a general formula (1-e) can be prepared by converting compound, R1 being nitro group among the compounds represented by the general formula (1-a), to reduced amino form (1-c) in an organic solvent such as ethanol, ethyl acetate or N,N-dimethylformamide at room temperature to under heating at ambient pressure to 329 kPa in the presence of catalyst such as palladium on carbon, followed by Meerwein arylation reaction, and further by reacting with NaSMe. Namely, the Meerwein arylation reaction can be conducted by diazotizing the amino form obtained by reduction with nitrite such as sodium nitrite in an organic solvent, for example, alcohol such as methanol or ethanol, ketone such as acetone or methyl ethyl ketone, water or mixture of these in the presence of hydrogen halide such as hydrochloric acid or hydrobromic acid, and then by reacting catalytic quantity of cuprous salt such as cuprous oxide or cuprous chloride in the presence of acrylamide or acrylic ester (methyl, ethyl, benzyl ester or the like). Further, the methylthio conversion can be performed by heating to by refluxing in an organic solvent, for example, alcohol solvent such as methanol or ethanol in the presence of NaSMe. Moreover, (1-e) being ester form can be derived to corresponding carboxylic acid form by hydrolyzing under a temperature condition of room temperature to refluxing in the presence of base such as lithium hydroxide, sodium hydroxide or potassium hydroxide or acid such as hydrochloric acid or sulfuric acid. Moreover, in the case of $X_2$ being acetylthio group in the general formula (1-d), this can be prepared by conducting Meerwein arylation reaction of amino form (1-c), and then by reacting with potassium thioacetate. The reaction can be performed at room temperature to 50° C. in an organic solvent, for example, tetrahydrofuran, dioxane or the like.

Compounds, $X_3$ being methylsulfinyl or methylsulfonyl in a general formula (1-f), and compounds represented by a general formula (1-g) can be prepared by oxidizing corresponding compound, $X_2$ being methylthio group in the general formula (1-d), and compounds represented by the general formula (1-e) using peroxide, respectively, and, if need be, by hydrolyzing. As the peroxide, aqueous hydrogen peroxide, perbenzoic acid, peracetic acid, m-chloroperbenzoic acid (mCPBA) or the like can be mentioned. The reaction can be performed under cooling with ice to at room temperature in an organic solvent, for example, methylene chloride, chloroform, ethyl acetate or the like. Moreover, the sulfonyl form (n=2) can be obtained directly using excess peroxide, but it can also be obtained by further oxidizing sulfinyl form (n=1) similarly after obtaining this. Moreover, the ester form can be derived to corresponding carboxylic acid form (1-g) by hydrolyzing under a temperature condition of room temperature to refluxing in the presence of base such as lithium hydroxide, sodium hydroxide or potassium hydroxide or acid such as hydrochloric acid or sulfuric acid. Similarly, in the case of $X_3$ being mercapto group in the general formula (1-f), it is possible to derive to corresponding mercapto form by hydrolyzing corresponding compound, $X_2$ being acetylthio group in the general formula (1-d), under a temperature condition of cooling with ice to room temperature in the presence of base such as lithium hydroxide, sodium hydroxide, potassium hydroxide or ammonia or acid such as hydrochloric acid or sulfuric acid.

Furthermore, the stereoisomer that can be seen in the sulfinyl form (1-f, n=1) can also be obtained by asymmetric oxidation, for example, by stereoselective oxidation using an optically active ligand such as Davis reagent (J. Am. Chem. Soc., 1992, 114, 1428) or a salen complex.

As the administering form of the inventive compounds, oral administration such as with tablet, capsule, granule, powder, inhalant, syrup or the like, or parenteral administration such as with injection, suppository or the like can be mentioned.

Best embodiment to put the invention into practice In following, the invention will be illustrated based on concrete examples, but the invention is not confined to these examples.

EXAMPLE 1

4-Methoxy-3-[N-(4-trifluoromethylbenzyl)carbamoyl]benzoic acid

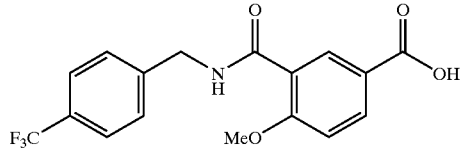

To a suspension of 1.00 g of 5-formyl-2-methoxybenzoic acid in 50 ml of methylene chloride were added 1.00 ml of triethylamine and 0.60 ml of ethyl chlorocarbonate, and the mixture was stirred for 15 minutes at room temperature. Then, a solution of 1.17 g of 4-trifluoromethylbenzylamine in 10 ml of methylene chloride was added and the mixture was stirred further for 3 hours at room temperature. After washed with water, the reaction mixture was dried over anhydrous sodium sulfate and the solvent was distilled off under reduced pressure. The residue obtained was purified by means of column chromatography (silica gel, hexane: ethyl acetate=1:1) and then recrystallized from a mixed solvent of diethyl ether-ethyl acetate-hexane to obtain 1.46 g of 5-formyl-2-methoxy-N-(4-trifluoromethylbenzyl)benzamide as colorless crystals.

Melting point 116–117° C. Elemental analysis (%) $C_{17}H_{14}F_3NO_3$ Calcd.(%) C, 60.54; H, 4.18; N, 4.15 Found (%) C, 60.80; H, 4.09; N, 4.28

To 500 mg of 5-formyl-2-methoxy-N-(4-trifluoromethylbenzyl)benzamide were added 20 ml of acetone and 0.5 ml of Jones reagent under cooling with ice, and the mixture was stirred for 25 minutes. Then, 0.2 ml of Jones reagent were added further and the mixture was stirred for 35 minutes. To the reaction mixture were added 100 ml of water, which was extracted (100 ml×2) with methylene chloride (small quantity of acetone was added). After washed with 50 ml of saturated brine, the organic layer was dried over anhydrous sodium sulfate. Solvent was distilled off under reduced pressure, and the residue obtained was purified by means of column chromatography (silica gel, methylene chloride:methanol=100:1, quantity of methanol was increased gradually), then recrystallized from hexane-acetone to obtain 270 mg of aimed product as white crystals.

Melting point 235.5–236.5° C., Mass analysis m/z 353 (M$^+$) Elemental analysis (%) $C_{17}H_{14}F_3NO_4$ Calcd.(%) C, 57.79; H, 3.99; N, 3.96 Found (%) C, 57.99; H, 3.95; N, 4.01

EXAMPLE 2

4-Methoxy-3-[N-(4-trifluoromethylbenzyl)]carbamoylphenylacetic acid

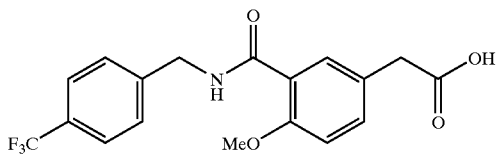

To 2.55 g of publicly known 5-cyanomethyl-2-methoxybenzoic acid were added 50 ml of dimethylformamide, 2.57 g of 4-trifluoromethylbenzylamine, 2.66 g of diethyl cyanophosphonate and 2.00 ml of triethylamine, and the mixture was stirred for 20 minutes under cooling with ice and for 6 hours at room temperature. The reaction mixture was poured into water and extracted with ethyl acetate. After washed with water, then with saturated brine, the organic layer was dried over anhydrous sodium sulfate. Solvent was distilled off under reduced pressure, and the residue was crystallized from hexane-diethyl ether and collected by filtration to obtain 4.44 g of 5-cyanomethyl-2-methoxy-N-(4-trifluoromethylbenzyl)benzamide as colorless crystals. Melting point 124–125° C. Elemental analysis (%) $C_{16}H_{15}F_3N_2O_2$ Calcd.(%) C, 62.07; H, 4.34; N, 8.04 Found (%) C, 62.03; H, 4.27; N, 7.99

To 484 mg of 5-cyanomethyl-2-methoxy-N-(4-trifluoromethylbenzyl)benzamide were added 10 ml of ethanol, 0.6 ml of 30% aqueous hydrogen peroxide and 5 ml of 0.1 mol/l sodium hydroxide, and the mixture was stirred for 1 hour at 50° C. Then, 0.6 ml of 30% aqueous hydrogen peroxide and 5 ml of 0.1 mol/l sodium hydroxide were added again and the mixture was stirred for 30 minutes at 50° C. The reaction mixture was poured into water and extracted with ethyl acetate. After washed with saturated aqueous solution of sodium bicarbonate and saturated brine in sequence, the organic layer was dried over anhydrous sodium sulfate. Solvent was distilled off under reduced pressure, and the residue obtained was purified by means of column chromatography (silica gel, methylene chloride:methanol=100:1 to 50:1) to obtain 318 mg of 5-carbamoylmethyl-2-methoxy-N-(4-trifluoromethylbenzyl)benzamide as colorless crystals.

Melting point 192–193° C. Elemental analysis (%) $C_{18}H_{17}F_3N_2O_3$ Calcd.(%) C, 59.02; H, 4.68; N, 7.65 Found (%) C, 58.87; H, 4.56; N, 7.63

To 700 mg of 5-carbamoylmethyl-2-methoxy-N-(4-trifluoromethylbenzyl)benzamide were added 21 ml of ethanol, 7 ml of 1 mol/l aqueous solution of sodium hydroxide, and the mixture was refluxed for 18 hours. The reaction mixture was poured into water, washed with ethyl acetate, and further the aqueous layer was adjusted to pH value of 1 to 2 with 2 mol/l hydrochloric acid, which was then extracted with ethyl acetate. The organic layer was washed with water and saturated brine in sequence and dried again over anhydrous sodium sulfate. Solvent was distilled off under reduced pressure, and the residue obtained was suspended with diethyl ether to collect the crystals by filtration. The crystals obtained were recrystallized from methylene chloride to obtain 435 mg of aimed product as colorless crystals.

Melting point 167–168° C. Elemental analysis (%) $C_{18}H_{16}F_3NO_4$ Calcd.(%) C, 58.86; H, 4.39; N, 3.81 Found (%) C, 58.72; H, 4.34; N, 3.86

EXAMPLE 3

5-[2-Carbamoyl-2-(methylthio)ethyl]-2-methoxy-N-(4-trifluoromethylbenzyl)benzamide

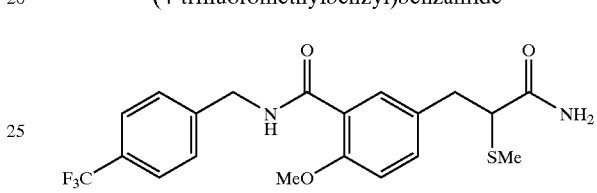

To a suspension of 17.2 g of 2-methoxy-5-nitrobenzoic acid in 35 ml of methylene chloride were added 35 ml of oxalyl chloride and one drop of dimethylformamide, and the mixture was stirred for 1 hour at room temperature. Solvent was distilled off under reduced pressure, 150 ml of dimethylformamide, 15 ml of triethylamine and 16.9 g of 4-trifluoromethylbenzylamine were added to the residue, and the mixture was stirred for 2 hours at room temperature. The reaction mixture was poured into water and extracted (150 ml×3) with ethyl acetate. The organic layer was washed with water and saturated brine in sequence and dried over anhydrous sodium sulfate. Solvent was distilled off under reduced pressure, and the residue obtained was crystallized from hexane:ethyl acetate=3:1, then the crystals were collected by filtration to obtain 26.6 g of 2-methoxy-5-nitro-N-(4-trifluoromethylbenzyl)benzamide as pale yellow crystals.

Melting point 108–109° C. Elemental analysis (%) $C_{16}H_{13}F_3N_2O_4$ Calcd.(%) C, 54.24; H, 3.70; N, 7.91 Found (%) C, 54.27; H, 3.73; N, 7.98

To 26.6 g of 2-methoxy-5-nitro-N-(4-trifluoromethylbenzyl)benzamide were added 270 ml of ethyl acetate and 2.6 g of 10% palladium on carbon under an atmosphere of argon, then argon was replaced with hydrogen gas, and the mixture was stirred for 8 hours at room temperature under an atmosphere of hydrogen gas. Catalyst was filtered through Celite(Hyflo Super-cel) and, after washed the collected material well with ethyl acetate, the filtrate was concentrated under reduced pressure. The residue obtained was purified by means of column chromatography (silica gel, ethyl acetate) to obtain 24.5 g of 5-amino-2-methoxy-N-(4-trifluoromethylbenzyl)benzamide as colorless crystals.

Melting point 115–117° C. Elemental analysis (%) $C_{16}H_{15}F_3N_2O_2$ Calcd.(%) C, 59.26; H, 4.66; N, 8.64 Found (%) C, 58.96; H, 4.57; N, 8.68

To a solution of 2.26 g of 5-amino-2-methoxy-N-(4-trifluoromethylbenzyl)benzamide in 27 ml of acetone and 11 ml of methanol were added 5.6 ml of 47% solution of hydrobromic acid, 540 mg of sodium nitrite and 2 ml of water under cooling with ice, and the mixture was stirred for 10 minutes. To the reaction mixture were added 3.00 g of acrylamide, and, after heated to 30° C., 135 mg of cupric oxide were added little by little, and the mixture was stirred further for 2 hours at 30° C. Solvent was distilled off under reduced pressure, and 25% aqueous ammonia was added to the residue, which was extracted with ethyl acetate. The organic layer was washed with water and saturated brine in sequence and dried over anhydrous sodium sulfate. Solvent was distilled off under reduced pressure, the residue obtained was crystallized from hexane:ethyl acetate=1:1, and then the crystals were collected by filtration to obtain 1.55 g of 5-(2-bromo-2-carbamoylethyl)-2-methoxy-N-(4-trifluoromethylbenzyl)benzamide as colorless crystals.

Melting point 192–193° C. Elemental analysis (%) $C_{19}H_{18}BrF_3N_2O_3$ Calcd.(%) C, 49.69; H, 3.95; N, 6.10 Found (%) C, 49.65; H, 3.82; N, 6.11

To 1.00 g of 5-(2-bromo-2-carbamoylethyl)-2-methoxy-N-(4-trifluoromethylbenzyl)benzamide were added 60 ml of ethanol and 200 mg of NaSMe, and, after refluxed for 3 hours, the mixture was allowed to stand overnight. Solvent was distilled off under reduced pressure, and water was added to the residue, which was extracted with methylene chloride. The organic layer was washed with saturated brine and dried over anhydrous sodium sulfate. Solvent was distilled off under reduced pressure, and the residue obtained was purified by means of column chromatography (silica gel, hexane:ethyl acetate=1:1) to obtain 865 mg of aimed product as colorless crystals.

Melting point 152.5–153.5° C. Elemental analysis (%) $C_{20}H_{21}F_3N_2O_3S$ Calcd.(%) C, 56.33; H, 4.96; N, 6.57 Found (%) C, 56.42; H, 4.97; N, 6.55

EXAMPLE 4

5-[2-Carbamoyl-2-(methylsulfinyl)ethyl]-2-methoxy-N-(4-trifluoromethylbenzyl)benzamide

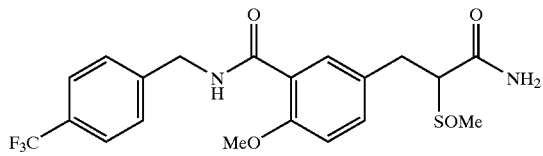

To 639 mg of 5-[2-carbamoyl-2-(methylthio)ethyl]-2-methoxy-N-(4-trifluoromethylbenzyl)benzamide were added 70 ml of methylene chloride and 368 mg of mCPBA under cooling with ice, and the mixture was stirred for 3 hours. The reaction mixture was washed with saturated aqueous solution of sodium bicarbonate and saturated brine in sequence and dried over anhydrous sodium sulfate. Solvent was distilled off under reduced pressure, and the residue obtained was purified by means of column chromatography (silica gel, methylene chloride:methanol=50:1 to 20:1) to obtain 486 mg of aimed product as colorless crystals.

Melting point 170–171° C. Elemental analysis (%) $C_{20}H_{21}F_3N_2O_4S$ Calcd.(%) C, 54.29; H, 4.78; N, 6.33 Found (%) C, 54.11; H, 4.72; N, 6.40

EXAMPLE 5

5-[2-Carbamoyl-2-(methylsulfonyl)ethyl]-2-methoxy-N-(4-trifluoromethylbenzyl)benzamide

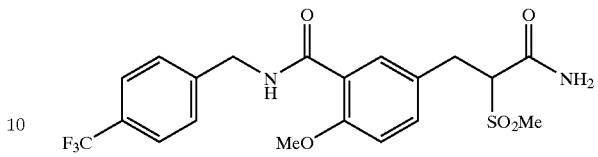

To 274 mg of 5-[2-carbamoyl-2-(methylsulfinyl)ethyl]-2-methoxy-N-(4-trifluoromethylbenzyl)benzamide were added 100 ml of methylene chloride and 155 mg of mCPBA, and the mixture was stirred for 3 hours. Saturated aqueous solution of sodium bicarbonate was added to the reaction mixture, and the insolubles were filtered off. The organic layer was washed with saturated aqueous solution of sodium bicarbonate and saturated brine in sequence and dried over anhydrous sodium sulfate. Solvent was distilled off under reduced pressure, and the residue obtained was purified by means of column chromatography (silica gel, methylene chloride:methanol=50:1 to 20:1) to obtain 201 mg of aimed product as colorless crystals.

Melting point 219–220° C. Elemental analysis (%) $C_{20}H_{21}F_3N_2O_5S$ Calcd.(%) C, 52.40; H, 4.62; N, 6.11 Found (%) C, 52.24; H, 4.52; N, 6.09

EXAMPLE 6

5-(2-Carbamoyl-2-mercaptoethyl)-2-methoxy-N-(4-trifluoromethylbenzyl)benzamide

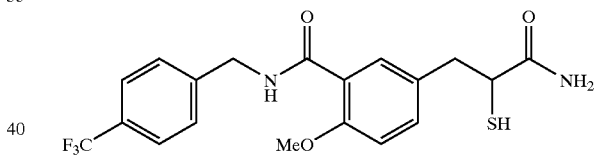

To 1.00 g of 5-(2-bromo-2-carbamoylethyl)-2-methoxy-N-(4-trifluoromethylbenzyl)benzamide were added 80 ml of tetrahydrofuran and 368 mg of potassium thioacetate under an atmosphere of argon, and the mixture was stirred for 6 hours at room temperature. Solvent was distilled off under reduced pressure, and ethyl acetate was added to the residue, which was washed with water and saturated brine in sequence and dried over anhydrous sodium sulfate. Solvent was distilled off under reduced pressure, and the residue obtained was crystallized from hexane-ethyl acetate, then the crystals were collected by filtration to obtain 904 mg of 5-(2-acetylthio-2-carbamoylethyl)-2-methoxy-N-(4-trifluoromethylbenzyl)benzamide as light brown crystals.

Melting point 159–161° C. Elemental analysis (%) $C_{21}H_{21}F_3N_2O_4S$ Calcd.(%) C, 55.50; H, 4.66; N, 6.16 Found (%) C, 55.32; H, 4.58; N, 6.18

To 300 mg of 5-(2-acetylthio-2-carbamoylethyl)-2-methoxy-N-)4-trifluoromethylbenzyl)benzamide were added 30 ml of saturated ammoniacal methanol under an atmosphere of argon, and the mixture was stirred for 3 hours at room temperature. Solvent was distilled off under reduced pressure, and the residue obtained was recrystallized from hexane-ethyl acetate to obtain 195 mg of aimed product as colorless crystals.

EXAMPLE 7

3-[4-Methoxy-3-[N-(4-trifluoromethylbenzyl)]carbamoylphenyl]-2-(methylthio)propionic acid

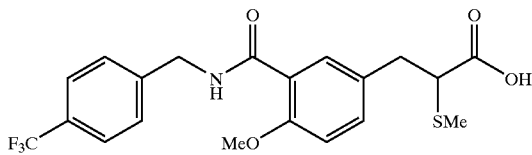

To a solution of 17.3 g of 5-amino-2-methoxy-N-(4-trifluoromethylbenzyl)benzamide in 170 ml of acetone and 85 ml of methanol were added 43 ml of 47% solution of hydrobromic acid and 17 ml of aqueous solution of 4.15 g of sodium nitrite under cooling with ice-salt, and the mixture was stirred for 10 minutes. To the reaction mixture were added 26 ml of methyl acrylate, and, after heated to 30° C., 1.04 g of cupric oxide were added little by little, and the mixture was stirred further for 1 hour at 40 to 50° C. Solvent was distilled off under reduced pressure, and 25% aqueous ammonia was added to the residue, which was extracted with ethyl acetate. The organic layer was washed with water and saturated brine in sequence and dried over anhydrous sodium sulfate. Solvent was distilled off under reduced pressure, and the residue obtained was crystallized from hexane-ethyl acetate, then the crystals were collected by filtration to obtain 10.3 g of methyl 2-bromo-3-[4-methoxy-3-[N-(4-trifluoromethylbenzyl)]carbamoylphenyl]-propionate as light brown crystals.

Melting point 110–111° C. Elemental analysis (%) $C_{20}H_{19}BrF_3NO_4$ Calcd.(%) C, 50.65; H, 4.04; N, 2.95 Found (%) C, 50.74; H, 3.86; N, 3.05

To 2.00 g of methyl 2-bromo-3-[4-methoxy-3-[N-(4-trifluoromethylbenzyl)]carbamoylphenyl]propionate were added 100ml of absolute methanol and 380 mg of NaSMe, and the mixture was refluxed for 6 hours. Solvent was distilled off under reduced pressure, and water was added to the residue, which was extracted with methylene chloride. The organic layer was washed with saturated brine and dried over anhydrous sodium sulfate. Solvent was distilled off under reduced pressure, and the residue obtained was purified by means of column chromatography (silica gel, hexane:ethyl acetate=1:1) to obtain 1.23 g of methyl 3-[4-methoxy-3-[N-(4-trifluoromethylbenzyl)]carbamoylphenyl]-2-(methylthio)propionate as colorless crystals.

Melting point 127–128° C. Elemental analysis (%) $C_{21}H_{22}F_3NO_4S$ Calcd.(%) C, 57.13; H, 5.02; N, 3.17 Found (%) C, 57.01; H, 4.91; N, 3.19

To 300 mg of methyl 3-[4-methoxy-3-[N-(4-trifluoromethylbenzyl)]-carbamoylphenyl]-2-(methylthio)propionate were added 7 ml of methanol and 3 ml of aqueous solution of 33 mg of lithium hydroxide, and the mixture was stirred for 1 hour at room temperature, then refluxed further for 5 hours. Solvent was distilled off under reduced pressure, and water was added to the residue, which was washed with diethyl ether. The aqueous layer was adjusted to pH value of 1 to 2 with 2mol/l hydrochloric acid and extracted with diethyl ether. After washed with water, the organic layer was dried over anhydrous sodium sulfate. Solvent was distilled off under reduced pressure, and the residue obtained was recrystallized from hexane-acetone to obtain 239 mg of aimed product as colorless crystals.

Melting point 170–171° C. Elemental analysis (%) $C_{20}H_{20}FNO_4S$ Calcd.(%) C, 56.20; H, 4.72; N, 3.28 Found (%) C, 56.14; H, 4.56; N, 3.20

EXAMPLE 8

3-[4-Methoxy-3-[N-(4-trifluoromethylbenzyl)]-carbamoylphenyl]-2-(methylsulfinyl)propionic acid (high-polarity form and low-polarity form)

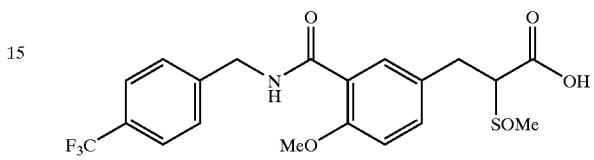

To 1.00 g of 3-[4-methoxy-3-[N-(4-trifluoromethylbenzyl)]-carbamoylphenyl]-2-(methylthio)propionic acid were added 20 ml of acetone, 600 mg of benzyl bromide and 490 mg of potassium carbonate, and the mixture was refluxed for 1 hour. The reaction mixture was poured into water and extracted with ethyl acetate. The organic layer was washed with water and saturated brine in sequence and dried over anhydrous sodium sulfate. Solvent was distilled off under reduced pressure, and the residue obtained was purified by means of column chromatography (silica gel, hexane:diethyl ether=5:1). After crystallized from hexane:diethyl ether, the crystals were collected by filtration to obtain 1.13 g of benzyl 3-[4-methoxy-3-[N-(4-trifluoromethylbenzyl)]carbamoylphenyl]-2-(methylthio)propionate as colorless crystals.

Melting point 77–79° C. Elemental analysis (%) $C_{27}H_{26}F_3NO_4S$ Calcd.(%) C, 62.66; H, 5.06; N, 2.71 Found (%) C, 62.72; H, 5.06; N, 2.76

To a solution of 1.00 g of benzyl 3-[4-methoxy-3-[N-(4-trifluoromethylbenzyl)]carbamoylphenyl]-2-(methylthio)-propionate in 20 ml of methylene chloride were added 429 mg of mCPBA under cooling with ice, and the mixture was stirred for 30 minutes. The reaction mixture was washed with saturated aqueous solution of sodium bicarbonate and saturated brine in sequence and dried over anhydrous sodium sulfate. Solvent was distilled off under reduced pressure, and the residue obtained was purified by means of column chromatography (silica gel, methylene chloride:methanol=100:1) to obtain 915 mg of diastereomer mixture of benzyl 3-[4-methoxy-3-[N-(4-trifluoromethylbenzyl)]carbamoylphenyl]-2-(methylsulfinyl)-propionate as colorless oily product. This diastereomer mixture was separated using high performance liquid chromatography (column: Inertsil ODS-2, column temperature: 25° C., mobile phase: acetonitrile:diluted phosphoric acid (1→1000)=1:1, 7.5 ml/min, measurement wavelength:240 nm), and respective eluate was extracted with methylene chloride and dried anhydrous sodium sulfate. Solvent was distilled off under reduced pressure, and respective residue obtained was purified by means of column chromatography (silica gel, methylene chloride:methanol=100:1) to obtain 383 mg of high-polarity benzyl ester form and 514 mg of low-polarity benzyl ester form.

High-polarity benzyl ester form: 400 MHz $^1$-NMR (CDCl$_3$) δ: 2.55 (1H, s, SOMe), 3.32(2H, d, J=8 Hz, CH$_2$CHS), 3.79(1H, t, J=8 Hz, CH$_2$CHS), 3.93(3H, s, OMe), 4.73(2H, d, J=6 Hz, CH₂N), 5.15(1H, d, J=12 Hz, OCH₂Ar), 5.22(1H, d, J=12 Hz, OCH₂Ar), 6.87(1H, d, J=8.4 Hz, ArH), 7.26–7.34(6H, m, ArH), 7.47(2H, d, J=8 Hz, ArH), 7.60(2H, d, J=8 Hz, ArH), 8.12(1H, d, J=2.4 Hz, ArH), 8.27(1H, t, J=6 Hz, CONH) High-resolution mass analysis C$_{27}$H$_{27}$F$_3$NO$_5$ (M+1): Calcd.:534.1562, Found 534.1592

Low-polarity benzyl ester form: 400 MHz $^1$H-NMR (CDCl$_3$) δ: 2.60 (1H, s, SOMe), 3.26(1H, dd, J=10.4, 14 Hz, CH$_2$CHS), 3.35(2H, dd, J=4.4, 14 Hz, CH$_2$CHS), 3.79(1H, dd, J=4.4, 10.4 Hz, CH$_2$CHS), 3.93(3H, s, OMe), 4.74 (2H, d, J=6 Hz, CH$_2$N), 5.13(2H, s, OCH$_2$Ar), 6.86(1H, d, J=8.8 Hz, ArH), 7.22–7.32(6H, m, ArH), 7.47(2H, d, J=8 Hz, ArH), 7.60(2H, d, J=8 Hz, ArH), 8.11(1H, d, J=3.2 Hz, ArH), 8.26(1H, t, J=6 Hz, CONH) High-resolution mass analysis C$_{27}$H$_{27}$F$_3$NO$_5$S(M+1): Calcd.: 534.1562, Found 534.1562

To 370 mg of benzyl 3-[4-methoxy-3-[N-(4-trifluoromethylbenzyl)]-carbamoylphenyl]-2-(methylsulfinyl)-propionate (high-polarity benzyl ester form) obtained by separation were added 20 ml of ethanol and 100 mg of 7.5% palladium on carbon (sulfur-tolerant) under an atmosphere of argon gas, then argon gas was replaced with hydrogen gas, and the mixture was stirred for 2 hours at room temperature under an atmosphere of hydrogen gas. Further, additions of 100 mg of 7.5% palladium on carbon (sulfur-tolerant) and stirrings of the mixture for 2 hours and for 1 hour were repeated, respectively, under an atmosphere of hydrogen gas to complete the reaction. Catalyst was removed by filtration, and the filtrate was concentrated under reduced pressure. The residue obtained was purified by means of column chromatography (silica gel, methylene chloride:ethyl acetate=50:1 to methylene chloride:methanol:acetic acid=50:1:1), then recrystallized from diethyl ether-acetone to obtain 176 mg of 3-[4-methoxy-3-[N-(4-trifluoromethylbenzyl)]-carbamoylphenyl]-2-(methylsulfinyl)propionic acid (high-polarity form) as colorless crystals.

Melting point 135–137° C. Test of purity by means of high performance liquid chromatography: 99% de (measuring conditions; column Inertsil ODS-3, φ4.6×250 mm, measurement wavelength 240 nm, flow rate 1.0 ml/min, mobile phase acetonitrile:diluted aqueous phosphoric acid (1→1000)=45:55, column temperature 30° C.) Elemental analysis (%) C$_{20}$H$_{20}$F$_3$NO$_5$S Calcd.(%) C, 54.17; H, 4.55; N, 3.16 Found (%) C, 53.94; H, 4.51; N, 3.13 400 MHz $^1$H-NMR(d$_6$-DMSO) δ: 2.66 (1H, s, SOMe), 3.05(1H, dd, J=5.5, 14 Hz, CH$_2$CHS), 3.10(1H, dd, J=10, 14 Hz, CH$_2$CHS), 3.85–3.93(4H, m, CH$_2$CHS, OMe), 4.57(2H, d, J=6 Hz, CH$_2$N), 7.10(1H, d, J=8.5 Hz, ArH), 7.37(1H, dd, J=2.4, 8.5 Hz, ArH), 7.54(2H, d, J=8 Hz, ArH), 7.66(1H, d, J=2.4 Hz, ArH), 7.70 (2H, d, J=8 Hz, ArH), 8.82(1H, t, J=6 Hz, CONH), 13.10(1H, br s, COOH)

Similarly, 480 mg of benzyl 3-[4-methoxy-3-[N-(4-trifluoromethylbenzyl)]carbamoylphenyl]-2-(methylsulfinyl)propionate (low-polarity benzyl ester form) obtained by separation were debenzylated reducibly to obtain 270 mg of 3-[4-methoxy-3-[N-(4-trifluoromethylbenzyl)]-carbamoylphenyl]-2-(methylsulfinyl)propionic acid (low-polarity form) as colorless crystals.

Melting point 127–128° C. High-resolution mass analysis C$_{20}$, H$_{21}$F$_3$NO$_5$S(M+1): Calcd.: 444.1093, Found 444.1090 400 MHz $^1$H-NMR(d$_6$-DMSO) δ: 2.68(1H, s, SOMe), 3.02 (1H, dd, J=10, 13.8 Hz, CH$_2$CHS), 3.11(1H, dd, J=4, 13.8 Hz, CH$_2$CHS), 3.86–3.91(4H, m, CH$_2$CHS, OMe), 4.57(2H, d, J=6 Hz, CH$_2$N), 7.11(1H, d, J=8.8 Hz, ArH), 7.38(1H, dd, J=2.4, 8.8 Hz, ArH), 7.54(2H, d, J=8 Hz, ArH), 7.66(1H, d, J=2.4 Hz, ArH), 7.70 (2H, d, J=8 Hz, ArH), 8.82(1H, t, J=6 Hz, CONH), 13.22(1H, br s, COOH) Test of purity by means of high performance liquid chromatography: 98%de (measuring conditions; column Inertsil ODS-3, φ4.6× 250mm, measurement wavelength 240 nm, flow rate 1.0 ml/min, mobile phase acetonitrile:diluted aqueous phosphoric acid (1→1000)=45:55, column temperature 30° C.)

EXAMPLE 9

3-[4-Methoxy-3-[N-(4-trifluoromethylbenzyl)] carbamoylphenyl]-2-(methylsulfonyl)propionic acid

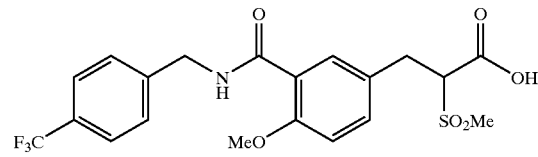

To a solution of 1.50 g of methyl 3-[4-methoxy-3-[N-(4-trifluoromethylbenzyl)]carbamoylphenyl]-2-(methylthio) propionate in 30 ml of methylene chloride were added 800 mg of mCPBA under cooling with ice, and the mixture was stirred for 30 minutes. The reaction mixture was washed with saturated aqueous solution of sodium bicarbonate and saturated brine in sequence and dried over anhydrous sodium sulfate. Solvent was distilled off under reduced pressure, and the residue obtained was purified by means of column chromatography (silica gel, methylene chloride:methanol=100:1 to 50:1) to obtain 1.22 g of methyl 3-[4-methoxy-3-[N-(4-trifluoromethylbenzyl)] carbamoylphenyl]-2-(methylsulfinyl)-propionate as colorless crystals. To a solution of 1.02 g of methyl 3-[4-methoxy-3-[N-(4-trifluoromethylbenzyl)]-carbamoylphenyl]-2-(methylsulfinyl)propionate obtained in 20 ml of methylene chloride were added 550 mg of mCPBA under cooling with ice, and the mixture was stirred for 7 hours at room temperature. The reaction mixture was washed with saturated aqueous solution of sodium bicarbonate and saturated brine in sequence and dried over anhydrous sodium sulfate. Solvent was distilled off under reduced pressure, and the crystals obtained were recrystallized from hexane-ethyl acetate to obtain 750 mg of methyl 3-[4-methoxy-3-[N-(4-trifluoromethylbenzyl)] carbamoylphenyl]-2-(methylsulfonyl)propionate as colorless crystals. Melting point 144–145° C.

Elemental analysis (%) C$_{21}$H$_{22}$F$_3$NO$_6$S Calcd.(%) C, 53.27; H, 4.68; N, 2.96 Found (%) C, 53.12; H, 4.48; N, 3.00

Into 6 ml of methanol were dissolved 300 mg of methyl 3-[4-methoxy-3-[N-(4-trifluoromethylbenzyl)] carbamoylphenyl]-2-(methylsulfonyl)propionate, 0.7 ml of 1 mol/l aqueous solution of sodium hydroxide were added, and the mixture was stirred for 1 hour at 50° C. The reaction mixture was poured into water and washed with diethyl ether. The aqueous layer was adjusted to pH value of 1 to 2 with 2 mol/l aqueous solution of hydrochloric acid, which was extracted with methylene chloride. The organic layer was washed with water and saturated brine in sequence and dried over anhydrous sodium sulfate. Solvent was distilled off under reduced pressure, and the crystals obtained were recrystallized from diethyl ether-ethyl acetate to obtain 218 mg of aimed product as colorless crystals.

Melting point 158–159° C. Elemental analysis (%) C$_{20}$H$_{20}$F$_3$NO$_6$S Calcd.(%) C, 52.29; H, 4.39; N, 3.05 Found (%) C, 52.11; H, 4.20; N, 3.05

Test Example 1

Test of transcriptional activation on peroxisome proliferator-activated receptors α and γ

To CHO cells cultured in a Ham's F-12 medium with 10% fetal calf serum, receptor plasmid that expresses fused protein of DNA-binding domain of GAL4 being transcription factor of yeast with ligand binding domain of human type PPARs α and γ (Biochemistry, 1993, 32, 5598), firefly luciferase reporter plasmid (Promega Corp.) that is activated by GAL4 and sea shiitake mushroom luciferase plasmid (Promega Corp.) for internal standard were cotransfected with lipofectamine. Thereafter, testing compound dissolved into dimethyl sulfoxide (DMSO) (final concentration of DMSO 0.1%) and control drug were adjusted with Ham's F-12 medium containing 10% defatted fetal calf serum to culture. After 24 hours, the luciferase activity was measured. Results are shown in table.

TABLE

| | Transcriptional activity |
|---|---|
| Example | PPARα $EC_{50}$ (μmol/l) |
| 3 | 2.1 |
| 7 | 1.2 |
| (8S)-HETE | 1.3 |

From these results, it was shown that the inventive compounds had potent transcriptional activity on human peroxisome proliferator-activated receptor.

Utilizability in the Industry

From the results as described above, it has become clear that the inventive novel o-anisamide derivatives have excellent human PPAR transcriptional activity. These compounds are useful for the prevention and therapy of metabolic diseases such as hyperlipidemia and diabetes, in which PPAR precipitates, as agonistic drugs on human PPAR.

What is claimed is:

1. An o-anisamide compound represented by a general formula (1)

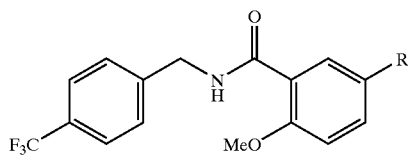

(1)

wherein R denotes a carboxyl group, carboxymethyl group or $CH_2CHXCOY$, wherein X denotes a mercapto group or $S(O)nMe$, n=0, 1 or 2, and Y denotes an amino group or hydroxyl group; or a medicinally acceptable salt or hydrate thereof.

2. The compound of claim 1, being 4-methoxy-3-[N-(4-trifluoromethylbenzyl)]carbamoylbenzoic acid.

3. The compound of claim 1, being 4-methoxy-3-[N-(4-trifluoromethylbenzyl)]carbamoylphenylacetic acid.

4. The compound of claim 1, being 5-[2-carbamoyl-2-(methylthio)ethyl]-2-methoxy-N-(4-trifluoromethyl-benzyl)benzamide.

5. The compound of claim 1, being 5-[2-carbamoyl-2-(methylsulfinyl)ethyl]-2-methoxy-N-(4-trifluoromethyl-benzyl)benzamide.

6. The compound of claim 1, being 5-[2-carbamoyl-2-(methylsulfonyl)ethyl]-2-methoxy-N-(4-trifluoromethyl-benzyl)benzamide.

7. The compound of claim 1, being 5-[2-carbamoyl-2-(mercapto)ethyl]-2-methoxy-N-(4-trifluoromethyl-benzyl)benzamide.

8. The compound of claim 1, being 3-[4-methoxy-3-[N-(4-trifluoromethylbenzyl)]carbamoylphenyl]-2-(methylthio)propionic acid.

9. The compound of claim 1, being 3-[4-methoxy-3-[N-(4-trifluoromethylbenzyl)]carbamoylphenyl]-2-(methylsulfinyl)propionic acid.

10. The compound of claim 1, being 3-[4-methoxy-3-[N-(4-trifluoromethylbenzyl)]carbamoylphenyl]-2-(methylsulfonyl)propionic acid.

11. An agonistic drug on human peroxisome proliferator-activated receptor (PPAR) comprising at least one o-anisamide compound represented by a general formula (1)

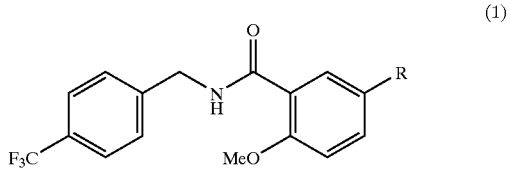

(1)

wherein R denotes a carboxyl group, carboxymethyl group or $CH_2CHXCOY$, wherein X denotes a mercapto group or $S(O)nMe$, n=0, 1 or 2, and Y denotes an amino group or hydroxyl group; or a medicinally acceptable salt or hydrate thereof, as effective ingredients.

12. A method of preventing or treating a metabolic disease in which peroxisome proliferator-activated receptor participates, in a subject, comprising administering the agonistic drug of claim 11 to said subject wherein said metabolic disease is at least one selected from the group consisting of hyperlipidemia and diabetes.

13. The method of claim 12, wherein the method is preventing and the disease is hyperlipidemia.

14. The method of claim 12, wherein the method is preventing and the disease is diabetes.

15. The method of claim 12, wherein the method is treating and the disease is hyperlipidemia.

16. The method of claim 12, wherein the method is treating and the disease is diabetes.

* * * * *